US00PP11805P2

(12) United States Plant Patent
Bartels

(10) Patent No.: US PP11,805 P2
(45) Date of Patent: Mar. 13, 2001

(54) PHLOX PLANT NAMED 'BARELEVEN'

(75) Inventor: Gosen B. H. Bartels, Aalsmeer (NL)

(73) Assignee: Bartels Breeding B.V., Aalsmer (NL)

( * ) Notice: Subject to any disclaimer, the term of this patent is extended or adjusted under 35 U.S.C. 154(b) by 0 days.

(21) Appl. No.: 09/328,635

(22) Filed: Jun. 9, 1999

(51) Int. Cl.[7] ..... A01H 5/00

(52) U.S. Cl. ..... Plt./320

(58) Field of Search ..... Plt./320

(56) References Cited

PUBLICATIONS

UPOV ROM GTITM Computer Database 2000/04, GTI JOUVE Retrieval Software, citations for 'Bareleven', Aug. 2000.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Phlox plant named 'Bareleven', characterized by its compact plant habit; suitability for potted plant production; short internodes; freely branching, dense and bushy growth habit; dark green foliage color; attractive soft pink flowers with reddish purple throat; and excellent postproduction longevity.

1 Drawing Sheet

BACKGROUND OF THE INVENTION

The present inventions relates to a new and distinct cultivar of Phlox plant, botanically known as *Phlox paniculata*, and hereinafter referred to by the cultivar name Bareleven.

The new Phlox is a product of a planned breeding program conducted by the Inventor in Aalsmeer, The Netherlands. The objective of the breeding program was to create new compact Phlox cultivars suitabe for potted plant production.

The new Phlox originated from a cross made by the Inventor of two proprietary Phlox seedling selections identified as code number 94.8 as the female, or seed, parent and 744.00.02 as the male, or pollen, parent. The cultivar Bareleven was discovered and selected by the Inventor as a flowering plant within the progeny of the stated cross in a controlled environment in Aalsmeer, The Netherlands, in 1995.

Plants of the new Phlox are more compact than plants of the female parent and differ in flower color. Plants of the new Phlox are more compact than plants of the male parent.

Asexual reproduction of the new cultivar by terminal cuttings taken at Aalsmeer, The Netherlands, has shown that the unique features of this new Phlox are stable and reproduced true to type in successive generations.

SUMMARY OF THE INVENTION

Plants of the cultivar Bareleven have not been observed under all possible environmental conditions. The phenotype may vary somewhat with variations in environment such as temperature, light intensity, daylength, and ferility level without, however, any variance in genotype.

The following traits have been repeatedly observed and are determined to be the unique characteristics of 'Bareleven'. These characteristics in combination distinguish 'Bareleven' as a new and distinct cultivar:

1. Compact plant habit, suitable for potted plant production; growth retardants are not required to maintain compact habit.

2. Freely branching and short internodes, dense and bushy growth habit.

3. Dark green foliage color.

4. Attractive soft pink flowers with reddish purple throat.

5. Excellent postproduction longevity.

Compared to plants of the *Phlox paniculata* cultivar Bright Eyes, not patented, plants of the new Phlox have shorter lateral branches with shorter internodes.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of typical plants of the new Phlox. Flower and foliage colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used.

Plants used for the description were grown in Aalsmeer, The Netherlands in a glass greenhouse under typical production conditions with day temperatures ranging from 16 to 28° C. and night temperatures ranging from 10 to 18° C. Plants used for the description were about 12 weeks old.

Botanical classification: *Phlox paniculata* cultivar Bareleven.

Parentage:

*Female parent.*—Proprietary *Phlox paniculata* selection identified as 94.8, not patented.

*Male parent.*—Proprietary *Phlox paniculata* selection identified as 744.00.02, not patented.

Propagation:

*Type.*—By cuttings.

*Time to initiate roots.*—Summer: About 21 days at 18° C. Winter: About 35 days at 18° C.

*Time to develop roots* (*time to produce a rooted liner*) .—Summer: About 28 days at 18° C. Winter: About 42 days at 18° C.

*Root description.*—Thick in diameter.

Plant description:

*Crop time.*—From cuttings, about 12 weeks are required to produce a finished flowering plant.

*Form.*—Compact, dense and busy perennial herb; plants typically do not require growth retardants to maintain compact habit. Typically grown as a potted plant, suitable for 13 to 17-cm containers.

*Plant height.*—About 40 cm.

*Plant width.*—About 35 cm.

*Vigor.*—Slow growth rate.

*Lateral branches.*—Quantity: Freely branching, pinching enhances lateral branch development; typically ten per plant. Lateral branch length: About 10 cm. Lateral branch diameter: About 8 cm. Internode length: About 1.5 cm. Color: 145A. Texture: Glabrous.

*Foliage description.*—Leaves simple, opposite, generally symmetrical, and long persisting. Tolerant to stresses, particularly drought. Quantity per lateral branch: Typically about 20. Length: About 8 cm. Width: About 4 cm. Shape: Oblong/elliptic. Apex: Sharply acute. Base: Rounded. Margin: Entire. Texture: Leathery. Color: Young foliage, upper surface: 141A. Young foliage, lower surface: 141A. Mature foliage, upper surface: 137A. Mature foliage, lower surface: 138A. Venation, upper surface: 137A. Venation, lower surface: 138A.

Flower description:

*Flower type and habit.*—Single round flowers arranged in terminal panicles, one per stem; flowers face upright. Panicles globular or pyramidal in shape. Freely flowering. Corolla, salverform, 5-lobed; calyx five-cleft. Flowers last about four days on the plant. Not persistent.

*Natural flowering season.*—Continuously flowering from July through September.

*Quantity.*—Very freely flowering with numerous flowers per panicle.

*Fragrance.*—Present; typical of species.

*Flower buds.*—Length: About 1 cm. Diameter: About 5 mm. Shape: Elliptic. Rate of opening: About one day.

*Flowers size.*—About 2 cm.

*Petals.*—Quantity: Five, fused. Length: About 2.5 cm. Width: About 1 cm. Shape: Broadly ovate. Apex: Rounded. Margin: Entire. Surface: Typically flat. Texture: Smooth. Color: Upper and lower surfaces, when opening and fully opened: 62D, color does not fade. Base of petals and flower throat (inside), fully opened: Reddish purple, close to 61A. Flower tube (outside), fully opened: Soft pink.

*Calyx.*—Shape: Campanulate; sepals, linear, fused at base. Sepal quantity: Five. Sepal apex: Acuminate. Sepal margin: Entire. Texture: Smooth. Color, upper and lower surfaces: 144A.

*Pedicel.*—Strength: Strong. Angle: About 45° to peduncle. Length: About 1 cm. Color: 145A.

*Reproductive organs.*—Pollen: Scarce. Pollen color: 2D. Pistil length: About 2.5 cm. Stigma shape: Trilobed. Stigma color: 154D. Style length: About 2.5 cm. Style color: 154D. Ovary color: 144A.

*Seed development.*—Seed development has not been observed.

Disease resistance: Under commercial conditions, resistance to Powdery Mildew has been observed.

It is claimed:

1. A new and distinct cultivar of Phlox plant named 'Bareleven', as illustrated and described.

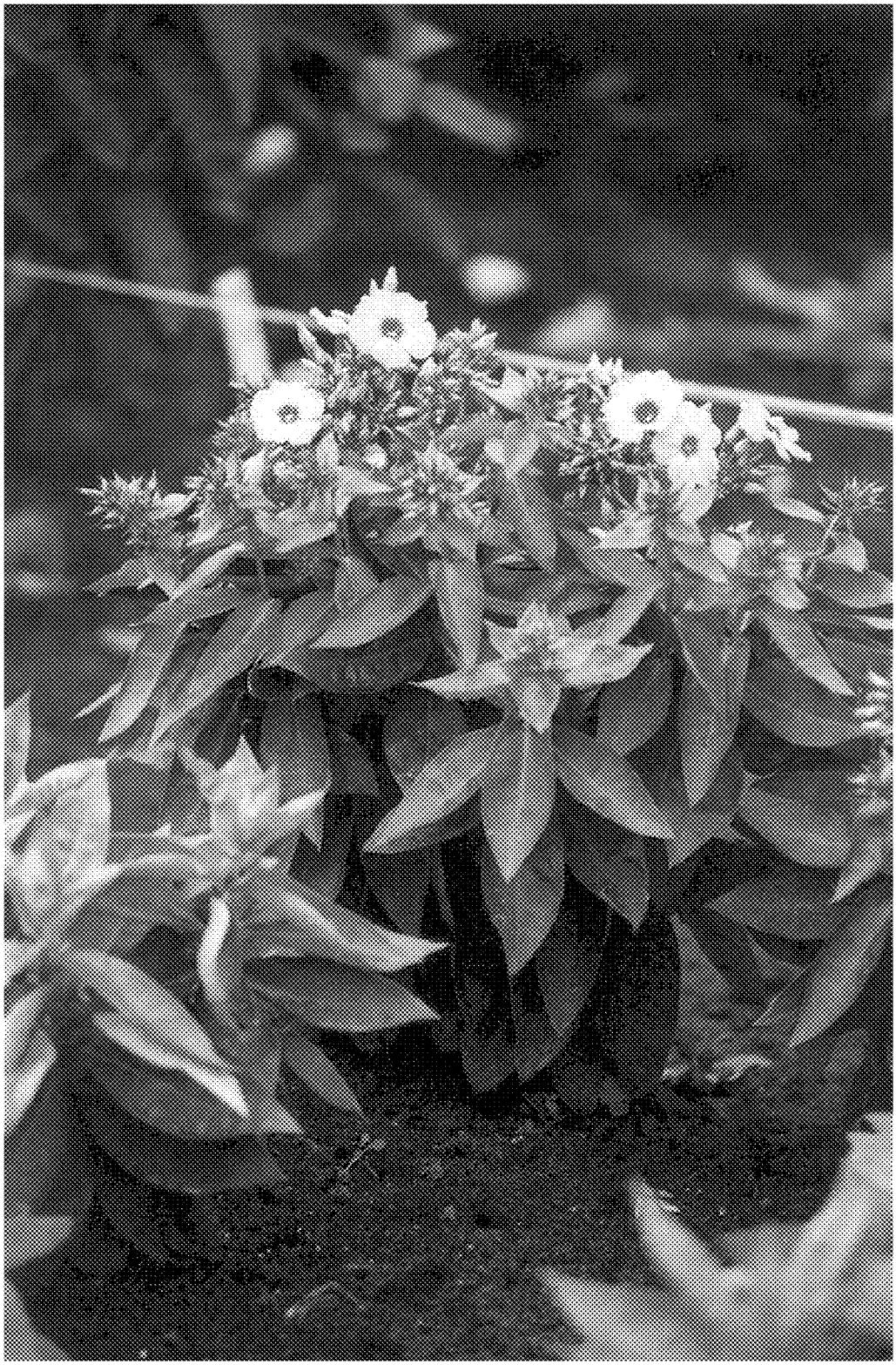

* * * * *